(12) United States Patent
Sawaya (10) Patent No.: US 9,694,030 B2
(45) Date of Patent: Jul. 4, 2017

(54) COMPOSITION FOR TREATMENT, INHIBITION AND ATTENUATION OF VIRUS

(71) Applicant: Frederick J. Sawaya, Farmington Hills, MI (US)

(72) Inventor: Frederick J. Sawaya, Farmington Hills, MI (US)

( * ) Notice: Subject to any disclaimer, the term of this patent is extended or adjusted under 35 U.S.C. 154(b) by 0 days.

(21) Appl. No.: 14/707,399

(22) Filed: May 8, 2015

(65) Prior Publication Data

US 2015/0238522 A1 Aug. 27, 2015

Related U.S. Application Data

(60) Provisional application No. 62/122,273, filed on Oct. 17, 2014.

(51) Int. Cl.
*A01N 59/02* (2006.01)
*A61K 33/04* (2006.01)

(52) U.S. Cl.
CPC .................................. *A61K 33/04* (2013.01)

(58) Field of Classification Search
USPC ......................................................... 424/709
See application file for complete search history.

(56) References Cited

U.S. PATENT DOCUMENTS 5,464,869 A * 11/1995 Travers ................ A61K 31/194
514/562
6,150,109 A * 11/2000 Edson ...................... C12N 7/00
435/236

FOREIGN PATENT DOCUMENTS

WO WO2004019682 * 3/2004

OTHER PUBLICATIONS

Hayden (Cardiovascular Diabetology 2005, 4:4).*
Machine translation of WO2004019682; Mar. 11, 2004.*
Adirekkiat (Nephrol Dial Transplant (2010)).*

* cited by examiner

*Primary Examiner* — Devang Thakor
(74) *Attorney, Agent, or Firm* — Barry Choobin; Patent 360

(57) ABSTRACT

The embodiments herein relate to a therapeutically active composition for the treatment, inhibition or attenuation of a virus. The composition comprises an effective amount of a sulfur containing compound along with one or more pharmaceutically acceptable carriers or excipients. The sulfur containing compound impairs a disulfide bond of a plurality of virus. The plurality of virus includes *Ebola* virus, herpes virus, dengue virus, smallpox virus, measles virus, mumps rubella virus, HIV (human immunodeficiency virus), Lassa fever virus and yellow fever virus, and even cancer, solid tumors, especially the fibrosarcoma tumor. The sulfur containing compound is sodium thiosulfate ($Na_2S_2O_3$) ("STS"). The composition is given orally, intravenously, inhalation, intravesical, vaginal, rectal, sublingual, ophthalmic, or topical.

6 Claims, 5 Drawing Sheets

FIG. 1

Signal Peptide  Mucin-like domain  Furin cleavage site

NH—[ GP 1 | | GP 2 ]—COOH
         └──── S-S ────┘
                        Transmembrane region

FIG. 2

Signal Peptide  Mucin-like domain  Furin cleavage site

NH— [ GP 1 | GP 2 ] —COOH

└——— S-S ———┘

Transmembrane region (STR) + (Na$_2$S$_2$O$_4$) = (SO$_2$) (S) (H$_2$S)

COMPOSITION FOR TREATMENT, INHIBITION AND ATTENUATION OF VIRUS

CROSS-REFERENCE TO RELATED PATENT APPLICATION

This patent application is entitled to the benefit of the filing date of provisional U.S. patent application Ser. No. 62/122,273 filed Oct. 17, 2014, under 35 USC 120.

BACKGROUND

Technical Field of Invention

The present invention generally relates to pharmaceutical medication composition for the treatment of viral infections, and particularly to an pharmaceutical formulation for treatment, inhibition and attenuation of viruses in human beings Description of Related Art A virus is a small infectious agent that replicates only inside the living cells of other organisms. Viruses can infect all types of life forms, from animals and plants to microorganisms, including bacteria and archaea. Ebola virus is one of five known viruses within the genus Ebolavirus. The four of the five known ebolaviruses, including EBOV, cause a severe and often fatal hemorrhagic fever in humans and other mammals, known as Ebola virus disease (EVD). Ebola virus has a fatality rate of 50-90% in humans. The Ebola virion is 80 nm in diameter and up to 1400 nm long. It contains both virus-encoded proteins and structures taken from the host cell.

Other viruses such as herpes, dengue, pox, measles, mumps rubella, HIV virus are made up of glycoprotein membrane, sulfur disulfide bonds and metal atoms. Mucin components are found in E. bola only, no other viruses have mucin. There is no other human safe drug which causes impairment of the glycoprotein components of the membranes of these viruses. Sulfur containing compounds have been proven for their effects on the impairment of S—S bonds and cause inhibition of the virus growth but none of the PRIOR sulfur containing compounds are human safe or truly antiviral.

The drug Bactrim is primarily antibacterial for the treatment of routine urinary tract infections. Bactrim contains a combination of sulfamethoxazole and trimethoprim. The Sulfamethoxazole and trimethoprim are both antibiotics that treat different types of infection caused by bacteria only.

Thus there is a need to develop a new and safer compound or drug which has a quality of impairing the disulfide bonds in viruses and causing the viruses inhibition, mutation, impairment and death. This occurs from the cellular level on upwards.

The above mentioned shortcomings, disadvantages and problems are addressed herein, as detailed below.

OBJECT OF THE INVENTION

The primary object of the embodiments herein is to provide a composition for the treatment, inhibition and attenuation of viruses, including viruses causing cancers and the cancers themselves.

Another object of the embodiments herein is to provide a composition comprising sulfur which has the capability of impairing the disulfide bonds and cause death of viruses, the viruses also includes cancer causing viruses.

Yet another object of the present invention is to provide a composition that can be given orally, parenterally, IV and PO, and topically.

Yet another object of the present invention is to provide a composition which is readily and cheaply available, easy to manufacture, and treats the viral infection.

These and other objects and advantages of the embodiments herein will become readily apparent from the following detailed description taken in conjunction with the accompanying drawings.

SUMMARY OF THE INVENTION

The various embodiments herein provide a therapeutically active composition for the treatment, inhibition or attenuation of a virus. The composition comprises an effective amount of a sulfur containing compound along with one or more pharmaceutically acceptable carriers or excipients. The sulfur containing compound impairs a disulfide bond of a plurality of virus. The plurality of virus includes Ebola virus, herpes virus, dengue virus, smallpox virus, measles virus, mumps rubella virus, HIV (human immunodeficiency virus), Lassa fever virus and yellow fever virus.

According to a preferred embodiment herein the virus is Ebola. The virus further comprises all other related viral infections and cancer viruses and cancer solid tumours as well. E. bola including Lassa fever virus, dengue-fever, Simian virus, yellowfever, small pox, Cancers for example gastric cancer, fibrosarcoma, pancreatic tumors, head and neck carcinomas. etc.

The sulfur containing compound is sodium thiosulfate ($Na_2S_2O_3$) ("STS").

The composition is given orally in the form of a tablet, powder, or a capsule.

The composition is given intravenously as an infusion of a solution containing STS.

The composition is given by inhalation, intravesical, vaginal, rectal, sublingual, ophthalmic, or topical.

The composition is topically administered in the form of a solution, cream, paste, or lotion containing STS.

The one or more pharmaceutically acceptable carriers or excipients is water.

The amount is between 1 mg and 2 g per kg of body weight per day of treatment.

According to another embodiment herein, a method for treatment, inhibition or attenuation of a virus, comprises administering an effective amount of a sulfur containing compound along with one or more pharmaceutically acceptable carriers or excipients. The sulfur containing compound impairs a disulfide bond of a plurality of virus. The plurality of virus includes Ebola virus, herpes virus, dengue virus, smallpox virus, measles virus, mumps rubella virus, HIV (human immunodeficiency virus), lassa fever virus and yellow fever virus.

The sulfur containing compound is sodium thiosulfate ("STS"). The sodium thiosulfate biodegrades amino acid polypeptide proteins and glycoproteins in a virus and releases $H_2S$ and $SO_2$ as breakdown products. The STS splits an S—S disulfide bond of a virus and disrupts integrity of an item, organism or cancer or infection. The splitting of the S—S disulfide bond and biodegrading the glycoprotein enables the STS to destroy a MUCIN protein, or prematurely release and disable MUCIN protein in the E. Bola virus. The destruction of said mucin protein saves a tetherin protein a said pateint's body and acts as a thetherin defence. The S—S bonds stretch and bend and make an E. bola virus mobile motorized folding and flexing bending. The STS ruins said S—S bonds and exposes Mucin protein, and said STS destroys *E. Bola* motor movements, and breaks the GP-S—S shield around the mucin. The STS attacks Mucin and dissolves it.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The other objects, features and advantages will occur to those skilled in the art from the following description of the preferred embodiment and the accompanying drawings in which.

DETAILED DESCRIPTION OF THE DRAWINGS

In the following detailed description, a reference is made to the accompanying drawings that form a part hereof, and in which the specific embodiments that may be practiced is shown by way of illustration. The embodiments are described in sufficient detail to enable those skilled in the art to practice the embodiments and it is to be understood that the logical, mechanical and other changes may be made without departing from the scope of the embodiments. The following detailed description is therefore not to be taken in a limiting sense.

In the following detailed description Sodium Thiosulfate, STS and $Na_2S_2O_3$ are used interchangeably referring to sodium thiosulfate. The term S—S bond refers to disulfide bonds, H2S refers to Hydrogen sulphide and SO2 refers to sulfur dioxide.

The various embodiment of the present invention relates to the fields of microbiology and antimicrobial pharmacotherapy. More particularly the compositions and methods of the invention relate to action of the active sulfur present in sodium thiosulfate that binds certain metals within polymerase or viral protein, or the breaking of the disulfide (S—S) bonds in glycoproteins or mucin with the resulting degradation of viral envelope structural integrity and reproductive function in the target virus.

According to an embodiment herein, a composition for treatment, inhibition and attenuation of viruses especially *Ebola* virus is provided. The composition provides a sulfur containing compound which is used in solid and liquid forms. The sulfur containing compound is sodium salt of sulfur. The sulfur containing compound is sodium thiosulfate (STS). The composition comprises sodium thiosulfate along with necessary additives.

The sulfur variation by products has the capability of impairing the disulfide bonds in viruses. In the human body, the sodium thiosulfate releases hydrogen sulfide, sulfur dioxide and S (sulphur atoms), and also forms $SO_3$-depending on the conditions. There are three sulfur atoms coming out of STS which eventually split S—S, digest protein amino acids, and dissolve the lethal MUCIN protein. STS uses its $H_2S$ primarily to bind with metals, even magnesium in Polymerase and zinc in VP-30 proteins. Furthermore, normally the S—S bonds act as hinges allowing movement in a virus, but the virus and lipid membrane is impaired in anchoring, moving, folding or replication by S—S bond splitting. $SO_2$ is also a by product of STS under certain conditions in the body. $SO_2$ also can vividly break disulfide bonds in a virus or in vitro.

Sodium thiosulfate is a sulfur-based pharmaceutical agent and proven to split S—S bonds, open the blood-brain barrier of the human for cancer drugs to work and treat hypertension in pregnancy.

STS is a colourless crystalline compound that is more familiar as the pentahydrate, $Na_2S_2O_3.5H_2O$, an efflorescent, monoclinic crystalline substance also called sodium hyposulfite. Sodium thiosulfate is produced chiefly from liquid waste products of sodium sulfide or sulfur dye manufacture. In the laboratory, this salt is prepared by heating an aqueous solution of sodium sulfate with sulfur or by boiling aqueous sodium hydroxide and sulfuric acid according to this equation:

$$6NaOH+4S \rightarrow 2Na_2S+Na_2S_2O_3+3H_2O$$

The human liver, kidneys and testes produce thiosulfate reductase, which catalyzes STS producing hydrogen sulfide ($H_2S$), as follows $Na_2S_2O_3$ always supplies the S—S Split Atoms & Molecules: HYRDOGEN SULFIDE PROOF of the use delivery of $H_2S$ from Na2S2O3 Thiosulfate is a potential respiratory electron acceptor for bacteria which live in anoxic environments or at the anoxic/oxic interface. The ability to respire thiosulfate is conferred by the enzyme thiosulfate reductase which catalyzes the reaction.

$$S_2O_3^{2-}+2H^++2e^- \rightarrow HS^-+HSO_3^-$$

$SO_2$ is also a by product of $Na_2S_2O_3$ under certain conditions in the body.

Furthermore, STS reacts with proteins, amino acids, and glycoproteins and produce hydrogen sulfide, $H_2S$ and sulfur dioxide, $SO_2$, which then degrades glycoprotein, and $H_2S$ & $SO_2$ continue by confusing the issue of sulfur replacement to the damaged finite disulfide bonds, by factoring infinite multiples of 6 electrons for every one sulfur damaged.

According to the embodiments herein, the safe sulfur containing compound is provided. The medically safe compound having the capability of splitting S—S bond is $Na_2S_2O_3$ (sodium thiosulfate, STS). At least 2 of the 3 three sulfurs coming out from STS reactions splits S—S bonds, digest protein amino acids, and dissolve lethal mucin (a unique feature of *E. bola*).

The self-regenerative properties of $Na_2S_2O_3$ to form $Na_2S_4O_6$, a tetrathionate is beneficial in self-regenerative available sulfur to destroy protein, bearing in mind that the human is immune to STS and is born with it as a metal eliminator and the reductase is inborn in liver, testes etc.

Viruses have biochemical structures in the viral envelope, in mucin, and in polymerase that are susceptible to attack by STS, or by the sulfur in $H_2S$ and $SO_2$. This is as follows: the glycoprotein of which viral envelopes are composed are stabilized by disulfide (S—S) bonds. STS (SO2 and H2S) break these disulfide bonds, and literally digest amino acids in the GP of *E. Bola*, and continue disrupting the viral envelope. Only *E. Bola* has MUCIN. *E. bola* viruses and viral families that are known to have an envelope composition that contains disulfide bonds and mucin.

Mucin, is a key agent in the ability of the *Ebola* virus to disable our immune system. It turns off our human cellular ALARM by blocking tetherin the "civil defense" alarm, thus facilitating the attachment of viral glycoprotein to target cells. This MUCIN-ATTACK is (can be) disrupted by hydrogen sulfide. In *Ebola*, polymerase must contain magnesium (Mg) in order for the virus to be infectious. Removing Mg from polymerase renders the *E. bola* virus non-lethal, and it behaves like the Marburg virus. STS by way of $H_2S$, which (can) capture Mg, producing $MgS_2O_3$ or MgS, respectively, render the polymerase inactive. The RNA tail section containing lethal kill magnesium section is called the 'PolyA'.

In addition, zinc-binding in VP-30 is required for *Ebola* transcription to occur. STS and $H_2S$ capture Zn, producing $ZnS_2O_3$ or ZnS, respectively, de-activating transcription. The disruption of zinc in Lassa fever is more profound than *E. bola*.

EXPERIMENTAL DETAILS

The top surface of *Ebola* virus is made up of glycoprotein. The glycoprotein (GP) has many aminoacids and a mucin component which is a glycoprotein similar to the beef broth. The study was conducted on beef broth solution.

The study using beef broth and sulfur (S) of $Na_2S_2O_3$ supports active sulfur binding of added copper and gas formation. The $H_2S/S/SO_2$ reactions were activated in the beef broth solutions by adding copper sulfate and $Na_2S_2O_3$ forming CuS. The sodium thiosulfate reacts with copper sulfate to form copper monosulfide, CuS, $H_2S$ and $SO_2$. The $H_2S$ alters amino acids in rat brains. The S, $H_2S$, $SO_2$ disrupt the lipid layer and is proven to disable S—S bonds and can cause protein degradation in an independent studies.

In 1981, the typhirium outbreak study of $Na_2S_2O_3$ using beef broth and pectin in *salmonella* released H2S from the Na2S2O3 was given. In 2009 Photolytic Experiment proved splitting of S—S bonds via H2S. The damage of $H_2S$ and $SO_2$ to bisulfide bonds is applicable to *Ebola*. In 2006 the Hampton report proved STS to cause protein degeneration. Other studies proved $H_2S$ damaging to viruses, and cancer viruses and cancer tumors as well. STS chemically binds to many metals, including heavy metals.

Due to intrinsic proven production of metal-binding sulfur and production of available $SO_2$ and $H_2S$, and $SO_3$ permits multiple viruses to be impaired or killed for use by the medical community to target any living virus with S—S bonds or any virus using zinc as building block in the virus. Magnesium is unique to *Ebola* which becomes non-lethal without it. Poly A is only poly A with Magnesium.

Humans produce thiosulfate reductase in the liver, kidneys, and testes. It is also believed to be produced within the mitochondria of the human cell itself. When STS encounters this enzyme, the reduction product is hydrogen sulfide; the $H_2S$ is the most aggressive form of binding sulfur on the earth which is human safe. STS is safe for all wildlife and it is also agriculturally safe while present in many food supplies/sources, and is unrestricted in agriculture USDA Law 2009. In humans with viral infection, the sulfur in hydrogen sulfide and in STS attacks and degrades certain biochemical components of the virus, including: dissolution of the disulfide couplets present in certain glycoproteins found in the viral envelope, thus disrupting viral envelope integrity; degrading mucin, thus hindering viral binding with CD4 cells; binding to magnesium in polymerase disabling viral RNA replication; binding to zinc in VP30 disabling transcription; attacking and degrading the cysteine found within the viral envelope, and lastly the attacking and disruption of S—S bond repairs in *E. bola* by STS-Eletron and Sulfur interferences The presence of these multiple attack points within numerous viruses render them susceptible to disruption by STS. The glycoprotein (GP), Zinc, and S—S bonds are common denominators of most killer viruses and some cancers.

According to the embodiments herein, the safe sulfur containing compound is provided. The medically safe compound has the capability of splitting S—S bond is $Na_2S_2O_3$ (sodium thiosulfate, STS). At least 2 of the 3 three sulfur atoms coming from STS reactions split S—S bonds, digest protein amino acids, and dissolve lethal mucin, a unique feature of *E. bola*. STS binds with metals, even magnesium in Polymerase and zinc in VP-30. The lipid membrane is impaired in anchoring, moving, folding or replication by S—S bond splitting. By paving the way for mutation and badly formed S—S bonds by releasing unneeded Sulfur atoms and electrons, thereby breeding confusion in the *E. bola* repair mechanism process.

According to the embodiments of the present invention, sodium thiosulfate leads to the S—S disulfide bond breakage and binds with Mg polymerase and Zn of VP30 of the virus, and dissolves S—S bonds of Mucin glycoprotein which mucin normally blocks/slimes/blinds the human cell so that tetherin viral alarm system fails and no immune response happens. Now the sulfur degraded MUCIN cannot block the human alarm system, tetherin. The interruption of Mg can halt RNA replication to human's lifespan's advantage, the introduction of exogenous aberrant Sulfur and electrons onto the *E. Bola* Repair-Bench-breeds mutations.

According to an embodiment of the present invention, the sodium thiosulfate can kill viruses selected from the group consisting of herpes, dengue, pox, measles, mumps rubella, or HIV, Lassa fever, Dengue fever and the cancer viruses, and solid cancer tumors a using cleavage of the diseases specialized disulfide bonds, especially. The cancer called "fibrosarcoma" and many or all solid cancer tumors other cancers treatable by H2S/STS situations are: those having an effect in breaking 'the disulfide bond between $Cys^{437}$ and $Cys^{542}$. The $Cys^{437}$ and $Cys^{542}$ are necessary for the secretion and activation of heparanase. The heparinase is a precursor to cancers'. The overexpression of heparanase— has been observed in many human tumor types, such as those in the head and neck pancreatic tumors, hepatocellular carcinoma, esophageal carcinoma and cultured human tumor cell lines.

The top surface of *Ebola* virus is made up of glycoprotein. The glycoprotein (GP) has many aminoacids, and a mucin component which is also a glycoprotein. The hydrogen sulfide ($H_2S$) in humans alters or ruins the amino acids in rat brains autopsies which are already proven. The STS disrupts the lipid layer and is proven to disable Sulfur-Sulfur (S—S) bonds in viruses. The STS also causes protein degradation in *Ebola* as well as other named viruses also according to the present invention.

The *Ebola* virus has an outer transmembrane layer made up of glycoprotein. It forms the trimers on the virion surface and mediates virus attachment and entry to the host cell. The viral membrane further contains proteins, such as components of the histocompatibily complex or other surface receptors, which in some cases can increase the infectivity of the enveloped viruses. The VP 40 and VP 24 are *Ebola* major and minor matrix proteins. They form a layer beneath the membrane and are crucial for virus binding. The *Ebola* RNA is packed with the NP protein. Together, they make a nucleocapsid-a spiral structure in the very centre of the virion. L stands for the large *Ebola* protein—the polymerase. It is responsible for the synthesis of the positive sense virus RNA. VP 35 and VP 30 are minor *Ebola* proteins. They act as interferon antagonists and transcription activation factors. The budding viral particle in the *Ebola* virus is wrapped in the lipid membrane taken from the human cell. The composition according to the present invention reacts with the zinc metal of VP 30 minor protein and disrupts. The viruses such as *E. bola*, Lassa, Dengue and Small Pox have zinc metal while *Ebola* has magnesium also. The sodium thiosulfate reacts with water and produces hydrogen disulfide (H2S) micro portions of gas inside the human body. $H_2S$ is referenced as being harmful to viral membrane integrity. $H_2S$ is proven to alter the amino acids in rat brain, (autopsies available). The smaller active sulfur binds faster to the metals of viruses and breaks the S—S disulfide bonds & cause protein degradation. $H_2S$ is referenced in 2009 Photoelectric Experiment as breaking S—S bonds. No protein, no peptide no amino acid is immune to $H_2S$ tenacious splitting—breaking of S—S bonds.

Figure 1:
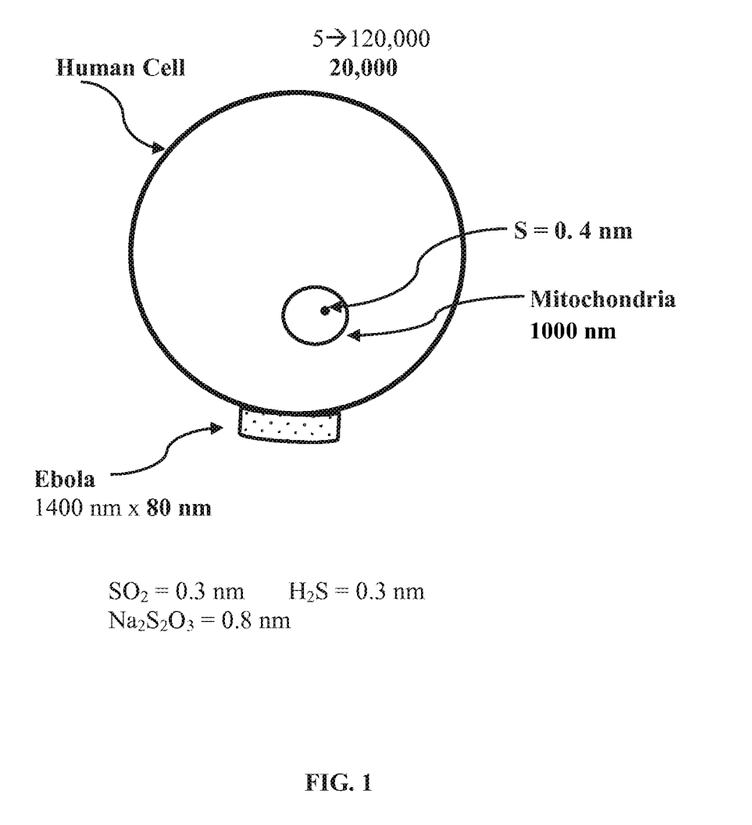
FIG. 1 is a conceptual drawing showing the binding of *Ebola* virus on a human cell, according to an embodiment herein.

FIG. 1 shows binding of *Ebola* virus on a human cell, according to an embodiment herein. With respect to FIG. 1, the $SO_2$ is 0.3 μm, $H_2S$ is 0.3 μm while sodium thiosulfate is 0.8 μm. The sulphur atom is shown as a back dot inside the mitochondria. The size of the mitochondria is 1000 nm while the Sulfur atom is 0.3-0.4 nm. The sulphur atom is small enough to safely enter Mitochondria which is 1000 nm in size. The size of the *Ebola* virus is 80 nm×1400 nm. Thus the sulphur atom enters the virus and destroys S—S bonds and digests glycoproteins also.

Figure 2:
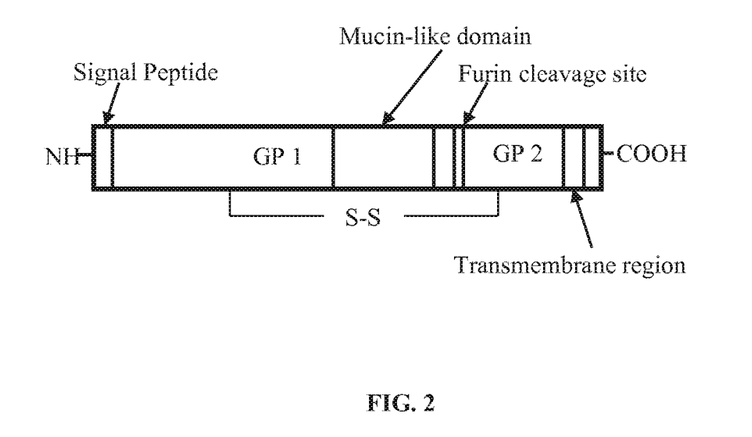
FIG. 2 shows *Ebola* gene code structure showing the S—S disulfide bond, according to an embodiment herein.

FIG. 2 shows *Ebola* gene code structure showing the S—S disulfide bond, according to an embodiment herein. With respect to FIG. 2, mucin domain and the transmembrane region are seen. The sodium thiosulfate binds the mucin protein and disrupts. STS also causes a premature release of mucin before it reaches the proper cell target thereby debilitating the mucin coating of the cell, by having caused its dislodging from between the S—S— bonds on either side of the MUCIN PLUG.

Figure 3:
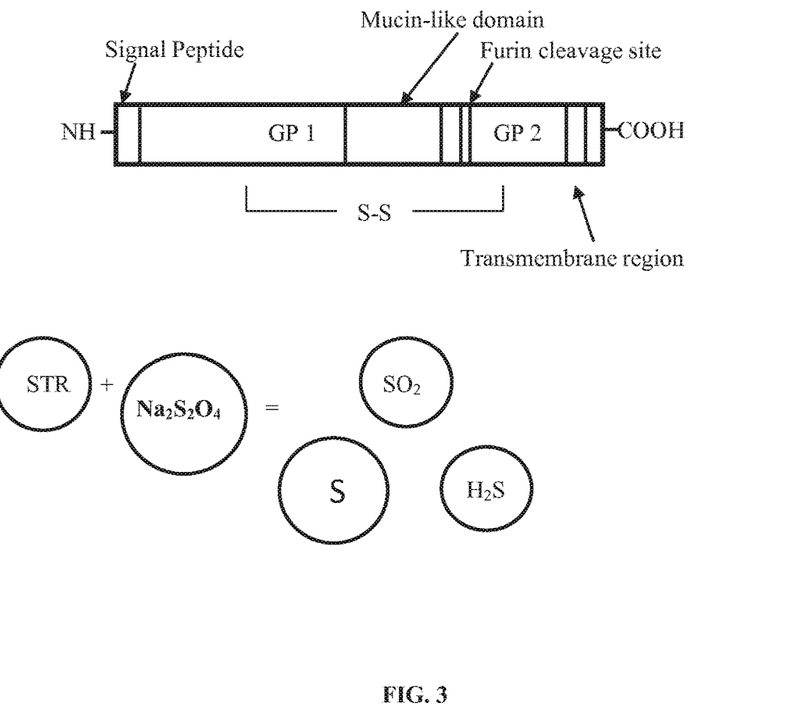
FIG. 3 shows chemical interactions of sodium thiosulfate reductase with sodium thiosulfate and S—S bonds, according to an embodiment herein.

FIG. 3 shows sodium thiosulfate illustrated below diagram of the *E. bola* virus gene structure in presence of sodium thiosulfate reductase enzyme, according to an embodiment of the present invention. The three (3) targets of H2S—SO2 are S—S bonds and MUCIN & METALS! STS is proven to biodegrade or prevent S—S bond formation [Hampton-2006]. regarding protein integrity and pharmaceuticals made of protein which are biodegradeably densitive. With respect to FIG. 3, the sodium thiosulfate reacts in presence of sodium thiosulfate reductase enzyme (STR) and releases hydrogen sulphide, sulphur and sodium dioxide. The reaction of $H_2S$ with the disulfide bonds shown near the MUCIN allows injury to the S—S bending mechanism and a premature loss of the Toxic MUCIN, which is cell specific and cannot block tetherin if it's mucin protein is floating free in the blood stream being chemically minced by STS. With respect to FIG. 3, the sodium thiosulfate ($Na_2S_2O_4$) reacts with water ($H_2O$) or dilutes gastric acid of the stomach or STR sodium thiosulfate reductase to produce $H_2S$ and $SO_2$. The $H_2S$ and $SO_2$ molecules react with glycoproteins, degrade mucin, and hinder the viral binding with CD4 cells. The $H_2S$ and $SO_2$ binds with magnesium in polymerase and disable the viral RNA replication, binds to zinc in VP30 and disable the transcription. The cysteine found within the viral envelope is also attacked and degraded. The presence of these multiple attack points within numerous viruses including *Ebola* virus renders them susceptible to disruption by STS. The S—S markings are the targets of a reducing agent and the VP30 containing zinc, and polymerase the replicator driver containing magnesium make the *Ebola* a good target for Sodium thiosulfate $Na_2S_2O_3$.

Furthermore almost all of the lethal and non lethal viruses and some microbes possess 1 2 or 3 of the salient contents-weak points of *Ebola*: namely a bind able metal (zinc) sulfur-degradable disulfide bonds and glycoprotein-amino acids & strategically placed S—S bonds and/or lipid membranes available to $H_2S$ & $SO_2$ both of which can both separate S—S bonds, and destroy amino acids protein. The trick of disruption, and biodegradation of a viral protein matrix or a microbe or other entity is that when a S—S bond breaks, it has a replacement waiting a sulfur. However, if competitive Sulfur atoms each with 8 electrons are crowding the delivery shelf, then the electron matching process is another ball game of protracted time and/or missing and non-replaced "S" parts. The confusion of choice in replacement of the broken—missing bond, will delay repair and leave a hole and vulnerability hopefully to further degradation.

Figure 4A:
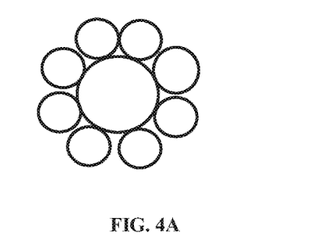
FIG. 4A shows a diagrammatic structure of the sulfur atom wherein centre circle is Sulfur (S) and the outer circles are electrons.
Figure 4B:
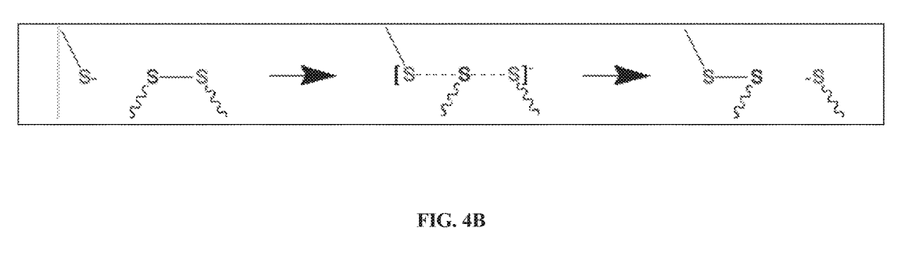
FIG. 4B shows Thiol-disulfide exchange showing the linear intermediate in which the charge is shared among the three sulfur atoms. The thiolate group (shown in red) attacks a sulfur atom (shown in blue) of the disulfide bond, displacing the other sulfur atom (shown in green) and forming a new disulfide bond.

Referring now to FIG. 4B, Thiol-disulfide exchange showing the linear intermediate in which the charge is shared among the three sulfur atoms. The thiolate group (shown in red) attacks a sulfur atom (shown in blue) of the disulfide bond, displacing the other sulfur atom (shown in green) and forming a new disulfide. A disulfide bond, also called an S—S bond, or disulfide bridge, is a covalent bond derived from two thiol groups. In biochemistry, the terminology R—S—S—R connectivity is commonly used to describe the overall linkages. The most common way of creating this bond is by the oxidation of sulfhydryl groups.

Figure 4C:
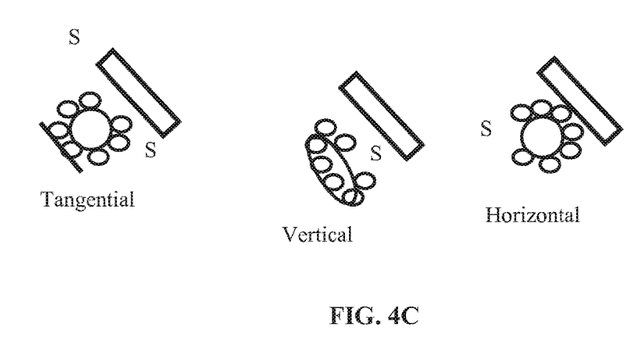
FIG. 4C shows three different positions of the electrons replacement.

FIG. 4C shows the various degrees for the sulfur atom replacement in a disulfide bond, according to an embodiment herein. With respect to FIG. 4C, the ideal replacement for a horizontal loss is a horizontal sulfur. If this horizontal replacement does not take place then a mutation happens. The *E. bola* has a lunch box tool kit which has the exact one which was lost but if interference occurs, the "Brain" of the damaged S═S bond can't figure out which Sulfur to accept and maybe already gets the S from $H_2S$ which is not aligned further the electrons from each sulfur are 8. So multiples of S outnumber the *E bola* sulfur atom replacement and confuse the issue. The S of $H_2S$ always chooses to destroy a bond, and not to bond at all to the disulfide bond. The missing sulfur can be replaced in multiple degrees such as vertical, horizontal and tangential etc, according to the formula x/360° alignment. The *Ebola* Virus has a reserve Sulfur bank, as do most Disulfide bond creatures have, but the sulphur to be replaced from the *ebola* 'tool box" would have to be the exact symmetry as the missing one, and ordinarily the replacement will happen with some positioning or juggling; however, delays or interferences (as caused by STS and S, $SO_2$, $H_2S$ will create mutations as described in the in Vitro studies of S—S bonding in the literature. The replacement at vertical and tangential degrees will not work if the missing Sulfur was horizontal for the sake of discussion, or will take some readjusting and time to fix the right position which can result in a mutation and death of the virus.

Figure 4D:
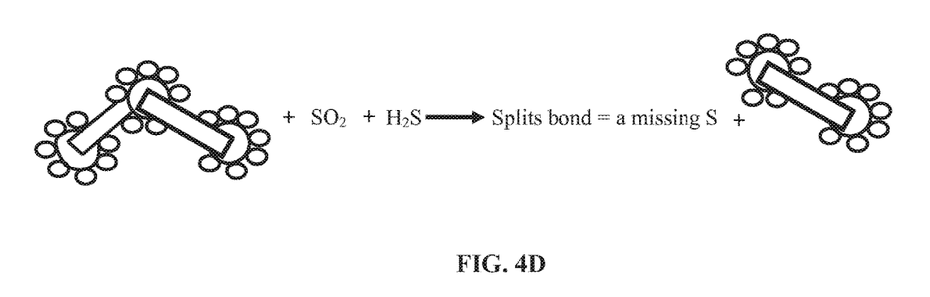
FIG. 4D shows a reaction wherein the sulfur dioxide and hydrogen sulphide reacts with the S—S bond, according to an embodiment herein.

Now referring to FIG. 4D, the reaction of sodium thiosulfate in presence of sodium thiosulfate reductase (STR) gives $H_2S$ and $SO_2$. $H_2S$ is relentless S—S bond splitter and so is $SO_2$. The enzyme sodium thiosulfate reductase is present in humans, white rats and mammals.

In *Ebola* replacement repair sulfur using $Na_2S_2O_3$ (i.e. $H_2S$ & $SO_2$) the alignment of the S atom is very necessary. The Degree of angulation is also mandatory. Instead of an amino acid or virus replacing its losses per habit systematically, random selection is presented to the empty sulfur slot, resulting in aberrant positioning and subsequent mutation or malfunctioning amino-acids or viruses or people's muscles, or viruses which won't grow, a Herpes virus that can not grow won't hurt you very long. Many more sulfurs compete with the designated replacement sulfur of *ebola*, and electronic confusion and mal positioning occurs resulting in mutation, and tissue or viral death. The reserve tank to its damaged disulfide bond is inhibited and competing with the sulfur of $Na_2S_2O_3$, the insertion of a misaligned electron in a escape graph results in mutation, damaged bonds, damaged proteins which damages the virus. The theory is to bombard the *Ebola* repair shop with misaligned sulfurs which selectively only break sulfur bonds disulfide (bi).

One sulphur is never alone and can be 6+ at a time creating 48 electrons from one composite. The repair of split S—S bonds is not simple. The complexity of S replacement as referring to electron alignment and the multiplicity of S and concomitant electrons to overwhelm the mechanics of the *Ebola* virus play a role in damaging the virus. The use of a multiple $Na_2S_2O_3$ which has Sulfur tetrathionate forming sulfurs each along with 4 modes of sulfur and 6-8 electrons per sulfur poses a serious unsolvable mathematical problem to any S—S bond repair virus or microbe. etc. The humans are born with $Na_2S_2O_3$ and bonds we are not broken by it. if the *Ebola* virus or any item has a repair slot of sulfurs, any major change lower or higher will alter the mechanic so lower number are not enough to repair, too many numbers such as 10 sulfurs are hanging around from a few $Na_2S_2O_3$ molecules that is 80 electrons. In all sorts of arrangements and positions to be adjusted for and the Virus or repairee cannot do it adequately. It involves the Sulfur and its 6-8 electrons positionally on $Na_2S_2O_3$ pose another variable in having 4 sulfurs forms available. $Na_2S_2O_3$ does so by adding multiple sulfur atoms i.e. 6-8 electrons/sulfur atom as variables unwanted and unexpected by the virus repair machine.

The repair in a split amino acid bond is dependent on electron alignment. Each sulfur has 8 electrons. So the missing slot needs just a set up to receive 8 electrons around the new Sulfur. If there is misalignment of electrons in the replacing sulfur in the broken S—S bond then hesitation, confusion and delays can occur. The $Na_2S_2O_3$ poses another variable in having 4 sulfurs forms available. Each sulfur has 8 electrons. So the missing slot needs just one sulfur to align correctly, not angled not backwards, not tangential, but figuratively-"exactly flush" i.e. the atom has to be horizontal. But any selected angle would likely be the best one comprising vertical, horizontal and tangential.

The Sulfur replacement of a broken-disulfide bond, S—S includes electron alignment as well. Each Sulfur has 6-8 electrons. Normally a split S—S is replaced by the S located in amino acids inventory. But the replacement has to be just like fitting 8 holes on a wheel fitting an 8 bolt axle. If the wheel is angled or tangential or horizontal in the wrong place electrons don't match. As if they came off the amino acid rack ready to install. You can't just throw a sulfur in an empty hole. There are 6 electrons to fit also. If the variables exists as below like (A) & (B) then the empty slot for sulfur is inconvenienced & confused (1) Too many sulfurs or (2) Too many electrons. The use of a multiple $Na_2S_2O_3$ which has Sulfur tetrathionate forming sulfurs each along with 4 modes of sulfur and 8 electrons per sulfur poses a serious unsolvable mathematical problem to any S—S bond repair virus or microbe etc. The humans are born with STS and S—S bonds but the S—S bonds in humans are immune to STS.

Table 1 Below Shows the Replacement of S Atoms

| Right-figure 4D | Left-figure 4D | Middle use figure # 4C |
|---|---|---|
| A sulfur missing (assume the lost sulfur was horizontally aligned. Shown in 4D | A normal sulfur horizontally repaired and replaced | 3 positions of S' receptor for S can be in just one of 3 positions. The donor (S) (8e) must match the receptor |

If the *Ebola* virus or any item has a repair slot of sulfurs. Any major change lower or higher alters the mechanics. Too low means not enough to repair, too many means if 10 sulfurs are hanging around from a few $Na_2S_2O_3$ molecules that is 80 electrons. In all sorts of arrangements and positions to be adjusted for and the Virus or repairee cannot do it adequately.

The size of the sodium thiosulfate atom is 0.8 nm. The size of sodium atom is 0.4 nm while the size of sulfur atom is 0.4 nm. The size of mitochondria is 1000 nm.

$$H_2S\text{=}H_2S\text{=}H_2S\text{=}\sim<0.300 \text{ nm} \tag{1}$$

$$SO_2\text{=}SO_2\text{=}SO_2\text{=}\sim<0.300 \text{ nm} \tag{2}$$

With respect to (1) and (2), the sizes of H2S and SO2 are approximately the same.

The sodium thiosulfate (STS) by-products combine to eventually reform STS after a series of simple steps. For example, SO2+SO2 will eventually reform STS after a series of simple steps.

Thus, the present invention provides a composition for the treatment of viral infections. The present invention provides a sodium containing compound for the inhibition of the viral infection. The present invention provides a therapeutic composition for the treatment, attenuation and inhibition of viruses in human body. The sodium containing compound inhibits the disulfide bonds in viruses and cancers and cause their death. The composition is easy to prepare and administer.

The monetary issue of the oral form allows affordable health and avoidance of death using the very inexpensive oral form makes the use of a vaccine possibly secondary not obsolete. No reported Fatalities in 22 years of IV use for Cyanide and Pregnancy-Ecclampsia. None. One oral dose or IV injection can manage many viruses vs-as opposed to a vaccine one or two at best, or the mmr. For the most part, much of the expense of creating a vaccine may be spared by using an IV drug 100% safe for Pregnant wife and unborn child.

The Oral ingestion of STS as a food preservative or salt additive or food supplement as done in Salt Packets, seems logical and safe for sure as shown in 2009 Federal Ruling USDA "Of Total Exemption of STS" from an restriction as an agricultural additive to fertilizer.

Furthermore almost all of the lethal and non lethal viruses and some microbes possess 1 2 or 3 of the salient contents-weak points of *Ebola*: namely a bind able metal (zinc) sulfur-degradable disulfide bonds and glycoprotein-amino acids & strategically placed S—S bonds and/or lipid membranes available to $H_2S$ & $SO_2$ both of which can both separate S—S bonds, and destroy amino acids protein. The trick of disruption, and biodegradation of a viral protein matrix or a microbe or other entity is that when a S—S bond breaks, it has a replacement waiting a sulfur. However, if competitive Sulfur atoms each with 8 electrons are crowding the delivery shelf, then the electron matching process is another ball game of protracted time and/or missing and non-replaced "S" parts The confusion of choice in replacement of the broken—missing bond, will delay repair and leave a hole and vulnerability hopefully to further degradation.

STS safely biodegrades amino acids polypeptides proteins and glycoproteins in any virus by mean of itself, $H_2S$ and $SO_2$ its main breakdown products. STS splits the bonds of any "any" S—S disulfide bond (virus infections or cancer or other) and disrupt the integrity of that item, organism, or cancer or infection. The splitting the S—S bonds and biodegrading the glycoprotein enables the STS to destroy MUCIN or prematurely release and disable MUCIN from *E. Bola*. The Tetherin is the body's signal to stop intruders, but mucin blocks all tetherin signals at the cellular level. So, by STS destroying mucin, or by changing its release position will save tetherin the body's first line of defense called tetherin. The S—S bonds stretch and bend and make the *E. bola* MOBILE motorized folding and flexing bending. STS ruins S—S bonds and exposes Mucin. STS destroys *E. Bola* motor movements, and breaks the GP, S—S shield around the MUCIN and can attack Mucin and dissolves it.

Thus as per the embodiments of the present invention, the multifunction of STS is provide. The STS kills diseases in three (3) main ways: (1) applications of metal binding abilities to impair protein synthesis and RNA replication of polymerase and (2) the S—S splitting ability of Na2S2O3 active ingredient H2S & SO2 which destroys and biodegrades all proteins. (3.) The sulphur electron competitive confusion entity factor wherein Extra unneeded electrons and sulphur disrupt the REPAIR PROCESS of *EBOLA* other Viruses and Cancers.

STS is the only medically safe way to bind metals in a virus using medication. STS is the only medically safe way to split S—S bonds and thereby destroy-degrade protein in viruses. STS impairs the protein synthesis and RNA replication of polymerase. $Na_2S_2O_3$ ($H_2S$, $SO_2$) is the most powerful prolific medically safe chemically active sulfur source on earth.

It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the claims.

I claim:

1. A method for treatment, inhibition or attenuation of a virus in a patient in need thereof, the method consisting of: administering an effective amount of sodium thiosulfate ($Na_2S_2O_3$) ("STS") and optionally one or more pharmaceutically acceptable carriers or excipients to the patient, wherein the STS impairs a disulfide bond of the virus, and wherein the virus is selected from the group consisting of *Ebola* virus, herpes virus, dengue virus, smallpox virus, measles virus, mumps rubella virus, lassa fever virus and yellow fever virus.

2. The method as claimed in claim 1, wherein the sodium thiosulfate ($Na_2S_2O_3$) ("STS") biodegrades amino acids, polypeptide proteins and glycoproteins in the virus and releases $H_2S$ and $SO_2$ as breakdown products.

3. The method as claimed in claim 2, wherein STS splits an S—S disulfide bond of the virus and disrupts viral envelope integrity by biodegrading the glycoprotein of the virus.

4. The method as claimed in claim 3, wherein said splitting the S—S disulfide bond and biodegrading the glycoprotein enables the STS to destroy a MUCIN protein in *Ebola* virus, or cause premature release of MUCIN protein and disable MUCIN protein in the *Ebola* virus.

5. The method as claimed in claim 4, wherein said destruction of said mucin protein saves tetherin protein in the human host from being blocked by the mucin protein.

6. The method as claimed in claim 2, wherein said STS disrupts said S—S disulfide bonds and exposes Mucin protein.

* * * * *